US 6,468,507 B1

(12) United States Patent
Cutie et al.

(10) Patent No.: US 6,468,507 B1
(45) Date of Patent: Oct. 22, 2002

(54) NON-AQUEOUS AEROSOL FORMULATION COMPRISING ROSIGLITAZONE MALEATE, A NON-AQUEOUS CARRIER, AND AN AMINO ACID STABILIZER

(75) Inventors: Anthony J. Cutie, Bridgewater, NJ (US); Akwete L. Adjei, Bridgewater, NJ (US); Frederick A. Sexton, Fair Haven, NJ (US)

(73) Assignee: Aeropharm Technology, Inc.

( * ) Notice: Subject to any disclaimer, the term of this patent is extended or adjusted under 35 U.S.C. 154(b) by 0 days.

(21) Appl. No.: 09/702,213

(22) Filed: Oct. 31, 2000

Related U.S. Application Data

(60) Provisional application No. 60/201,564, filed on May 1, 2000.

(51) Int. Cl.[7] .................. A61M 11/00; A61M 18/00; A61P 7/12; A01N 25/06; A61K 9/12
(52) U.S. Cl. .............. 424/45; 424/44; 424/43; 514/4; 514/866; 128/200.14; 128/200.21; 128/200.23
(58) Field of Search .............. 424/45, 44, 43; 514/4, 866; 128/200.14, 200.21, 200.23

(56) References Cited

U.S. PATENT DOCUMENTS

| 5,011,678 A | 4/1991 | Wang et al. |
|---|---|---|
| 5,594,015 A | 1/1997 | Kurtz et al. |
| 5,635,159 A | 6/1997 | Fu Lu et al. |
| 5,744,123 A * | 4/1998 | Akehurst et al. .......... 424/45 |
| 6,136,294 A * | 10/2000 | Adjei et al. .......... 424/45 |
| 6,193,954 B1 | 2/2001 | Adjei et al. |

FOREIGN PATENT DOCUMENTS

| WO | WO 90 009781 A | 9/1990 |
|---|---|---|
| WO | WO 96 19198 A | 6/1996 |
| WO | WO-98/57636 A1 * | 12/1998 |

OTHER PUBLICATIONS

Paterniti et al., WO 9805331 A2, Prevention or Treatment of Type 2 Diabetes or Cardiovascular Disease with PPAR Modulators, Feb. 12, 1998, abstract.*

Patton et al., Advanced Drug Delivery Reviews, 8(1992) 179–196.

* cited by examiner

*Primary Examiner*—Frederick Krass
*Assistant Examiner*—Clinton Ostrup
(74) *Attorney, Agent, or Firm*—Frommer Lawrence & Haug LLP

(57) ABSTRACT

A non-aqueous medicinal aerosol formulation comprising rosiglitazone maleate, a fluid carrier, and an amino acid stabilizer. The aerosol formulation may also include drug combination formulations comprising rosiglitazone maleate and a second anti-diabetic medicament.

21 Claims, No Drawings

NON-AQUEOUS AEROSOL FORMULATION COMPRISING ROSIGLITAZONE MALEATE, A NON-AQUEOUS CARRIER, AND AN AMINO ACID STABILIZER

This application claims priority from U.S. provisional application Ser. No. 60/201,564 filed May 1, 2000, which is incorporated herein by reference.

BACKGROUND OF THE INVENTION

1. Field of the Invention

This invention relates to a medicinal aerosol formulation, and more particularly, to a medicinal aerosol formulation comprising rosiglitazone maleate and a protective colloid stabilizer.

2. Description of the Related Art

Delivery of drugs to the lung by way of inhalation is an important means of treating a variety of conditions, including such common local conditions as cystic fibrosis, pneumonia, bronchial asthma and chronic obstructive pulmonary disease and some systemic conditions including pain management, immune deficiency, hormonal therapy, erythropoiesis, diabetes, etc. Anti-diabetic drugs, e.g. an insulin, are among the drugs that are administered to the lung for such purposes. Such drugs are commonly administered to the lung in the form of an aerosol of particles of respirable size (less than about 10 µm in diameter). In order to assure proper particle size in the aerosol, particles can be prepared in respirable size and then incorporated into a colloidal dispersion containing either a propellant, as a pressurized metered dose inhaler (MDI), or air such as is the case with a dry powder inhaler (DPI). Alternatively, formulations can be prepared in solution or emulsion form in order to avoid the concern for proper particle size in the formulation. Solution formulations must nevertheless be dispensed in a manner that produces particles or droplets of respirable size.

For MDI preparations, once prepared, the aerosol formulation is filled into an aerosol canister equipped with a metered dose valve. In the hands of the patient the formulation is dispensed via an actuator adapted to direct the dose from the valve to the patient.

What is needed and desired is a stable aerosol formulation for the treatment of diabetes and conditions related thereto comprising rosiglitazone maleate.

SUMMARY OF THE INVENTION

It has surprisingly been found that novel and stable medicinal aerosol formulations of rosiglitazone maleate can be obtained without the use of either cosolvents, such as ethanol, or surfactants, such as sorbitan trioleate which are typically added to a binary aerosol formulation. Such stable medicinal aerosol formulations are obtained by the use of a protective colloid stabilizer.

DETAILED DESCRIPTION OF THE INVENTION

This application makes reference to U.S. application Ser. No. 09/158,369 filed Sep. 22, 1998, now U.S. Pat. No. 6,136,294, which is issued on Oct. 24, 2000 which is incorporated hereinto by reference in its entirety.

This invention involves a stable suspension aerosol formulation suitable for pressurized delivery which comprises (1) rosiglitazone maleate, (2) a suitable propellant, and (3) a suitable stabilizer.

Rosiglitazone maleate or any of its derivatives such as the maleate, is a suitable medicament or drug which is suitable for administration by inhalation, the inhalation being used for oral and nasal inhalation therapy. A stable, colloidal dispersion of the medicament in a fluid, e.g. air, hydrocarbon gases, chlorofluorocarbon (CFC) propellants or non-CFC propellants, such as tetrafluoroethane (HFA-134a) and heptafluoropropane (HFA-227) is described.

A stabilizer of a polyionic species, such as an amino acid and a small molecule peptide, as inactive formulation components which trigger loss of adhesive bond strength between the medicament particles is employed. An electret or sterially stabilized aerocolloid particles of the selected medicaments is thus formed. Electrets are the electrostatic equivalent of permanent magnets but can be susceptible to breakdown in the presence of moisture, such as that present in air or at ambient humidity conditions of the respiratory tract. Accordingly the present invention applies to dry powder aerosols, portable nebulizer systems, as well pressurized metered dose inhaler formulations.

The resultant aerocolloid is chemically and physically stable and can remain in suspension until the particles of rosiglitazone maleate reach the alveolar or other absorption sites in the airways of a patient, e.g. human, animal, being treated. Once at the absorption site, the particles of rosiglitazone maleate should be efficiently trapped at the deposition site as a result of moisture in the ambient, dissolve rapidly in the epithelial lining fluids, and be absorbed quickly across the biomembranes of the patient, thereby limiting possible deactivation by metabolizing enzymes in the airways.

Rosiglitazone maleate to which the subject invention is directed forms a stable dispersion suitable for delivery to a patient, e.g., human or animal. Rosiglitazone maleate alone can be delivered to the patient or it can be combined with another suitable anti-diabetic agent selected from an acetohexamide, chlorpropamide, tolazemide, tolbutamide, glipizide, glyburide, glucophage, phentolamine, etc., and a mixture of any two or three of the foregoing medicaments or other medicaments. Typically, additional medicaments combined with rosiglitazone, alone or combined with another suitable anti-diabetic agent, include a peptide, polypeptide, or protein biotherapeutic ranging from 0.5 K Dalton to 150 K Dalton in molecular size. In particular, the peptide, polypeptide, or protein biotherapeutic medicament includes diabetic aids; insulins and insulin analogs; amylin; glucagon; surfactants; immunomodulating peptides such as cytokines, chemokines, lymphokines, interleukins such as taxol, interleukin-1, interleukin-2, and interferons; antibiotics and other antiinfectives; hormones and growth factors; enzymes; vaccines; immunoglobulins; vasoactive peptides; antisense agents; genes, oligonucleotides, and nucleotide analogs.

The term diabetic aid includes natural, synthetic, semi-synthetic and recombinant medicaments such as activin, glucagon, insulin, somatostatin, proinsulin, amylin, and the like.

The term "insulin" shall be interpreted to encompass natural extracted human insulin, recombinantly produced human insulin, insulin extracted from bovine and/or porcine sources, recombinantly produced porcine and bovine insulin and mixtures of any of these insulin products. The term is intended to encompass the polypeptide normally used in the treatment of diabetics in a substantially purified form but encompasses the use of the term in its commercially available pharmaceutical form, which includes additional excipients. The insulin is preferably recombinantly produced and may be dehydrated (completely dried) or in solution.

The terms "insulin analog," "monomeric insulin" and the like are used interchangeably herein and are intended to encompass any form of "insulin" as defined above wherein one or more of the amino acids within the polypeptide chain has been replaced with an alternative amino acid and/or wherein one or more of the amino acids has been deleted or wherein one or more additional amino acids has been added to the polypeptide chain or amino acid sequences which act as insulin in decreasing blood glucose levels. In general, the "insulin analogs" of the present invention include "insulin lispro analogs," as disclosed in U.S. Pat. No. 5,547,929, incorporated hereinto by reference in its entirety; insulin analogs including LysPro insulin and humalog insulin, and other "super insulin analogs", wherein the ability of the insulin analog to affect serum glucose levels is substantially enhanced as compared with conventional insulin as well as hepatoselective insulin analogs which are more active in the liver than in adipose tissue. Preferred analogs are monomeric insulin analogs, which are insulin-like compounds used for the same general purpose as insulin such as insulin lispro i.e., compounds which are administered to reduce blood glucose levels.

The term "amylin" includes natural human amylin, bovine, porcine, rat, rabbit amylin, as well as synthetic, semi-synthetic or recombinant amylin or amylin analogs including pramlintide and other amylin agonists as disclosed in U.S. Pat. Nos. 5,686,411, and 5,854,215, both of which are incorporated hereinto by reference in their entirety.

The term "immunomodulating proteins" include cytokines, chemokines, lymphokines complement components, immune system accessory and adhesion molecules and their receptors of human or non-human animal specificity. Useful examples include GM-CSF, IL-2, IL-12, OX40, OX40L (gp34), lymphotactin, CD40, CD40L. Useful examples include interleukins for example interleukins 1 to 15, interferons alpha, beta or gamma, tumour necrosis factor, granulocyte-macrophage colony stimulating factor (GM-CSF), macrophage colony stimulating factor (M-CSF), granulocyte colony stimulating factor (G-CSF), chemokines such as neutrophil activating protein (NAP), macrophage chemoattractant and activating factor (MCAF), RANTES, macrophage inflammatory peptides MIP-1a and MIP-1b, complement components and their receptors, or an accessory molecule such as B7.1, B7.2, ICAM-1, 2 or 3 and cytokine receptors. OX40 and OX40-ligand (gp34) are further useful examples of immunomodulatory proteins. Immunomodulatory proteins can for various purposes be of human or non-human animal specificity and can be represented for present purposes, as the case may be and as may be convenient, by extracellular domains and other fragments with the binding activity of the naturally occurring proteins, and muteins thereof, and their fusion proteins with other polypeptide sequences, e.g. with immunoglobulin heavy chain constant domains. Where nucleotide sequences encoding more than one immunomodulating protein are inserted, they can for example comprise more than one cytokine or a combination of cytokines and accessory/adhesion molecules.

The term "interferon" or "IFN" as used herein means the family of highly homologous species-specific proteins that inhibit viral replication and cellular proliferation and modulate immune response. Interferons are grouped into three classes based on their cellular origin and antigenicity, alpha-interferon (leukocytes), beta-interferon (fibroblasts) and gamma-interferon (immunocompetent cells). Recombinant forms and analogs of each group have been developed and are commercially available. Subtypes in each group are based on antigenic/structural characteristics. At least 24 interferon alphas (grouped into subtypes A through H) having distinct amino acid sequences have been identified by isolating and sequencing DNA encoding these peptides. See also Viscomi, 1996 Biotherapy 10:59–86, The terms "alpha.-interferon", "alpha interferon", "interferon alpha", "human leukocyte interferon" and IFN are used interchangeably herein to describe members of this group. Both naturally occurring and recombinant alpha interferons, including consensus interferon such as that described in U.S. Pat. No. 4,897,471, the contents of which are incorporated hereinto by reference in its entirety, may be used in the practice of the invention. Human leukocyte interferon prepared in this manner contains a mixture of human leukocyte interferons having different amino acid sequences. Purified natural human alpha interferons and mixtures thereof which may be used in the practice of the invention include but are not limited to Sumiferon RTM interferon alpha-n1 available from Sumitomo, Japan; Welfferong interferon alpha-n1 (Ins) available from Glaxo-Wellcome Ltd., London, Great Britain; and Alferon RTM interferon alpha-n3 available from the Purdue Frederick Co., Norwalk, Conn.

The terms "anti-proteases" and "protease-inhibitors" are used interchangeably and apply to synthetic, semi-synthetic, recombinant, naturally-occurring or non-naturally occurring, soluble or immobilized agents reactive with receptors, or act as antibodies, enzymes or nucleic acids. These include receptors which modulate a humoral immune response, receptors which modulate a cellular immune response (e.g., T-cell receptors) and receptors which modulate a neurological response (e.g., glutamate receptor, glycine receptor, gamma-amino butyric acid (GABA) receptor). These include the cytokine receptors (implicated in arthritis, septic shock, transplant rejection, autoimmune disease and inflammatory diseases), the major histocompatibility (MHC) Class I and II receptors associated with presenting antigen to cytotoxic T-cell receptors and/or T-helper cell receptors (implicated in autoimmune diseases) and the thrombin receptor (implicated in coagulation, cardiovascular disease). The list also includes antibodies which recognize self-antigens such as those antibodies implicated in autoimmune disorders and antibodies which recognize viral (e.g., HIV, herpes simplex virus) and/or microbial antigens.

The terms "hormones" and "growth factors" include hormone releasing hormones such as growth hormone, thyroid hormone, sourced from natural, human, porcine, bovine, ovine, synthetic, semi-synthetic, or recombinant sources. These also include somatostatin analogs such as octreotide (Sandostatin), medicaments for respiratory disorders (e.g., superoxide dismutase), RDS (e.g., surfactants, optionally including apoproteins), and the like.

Examples of biological molecules for which lead molecules can be synthesized and selected and combined with rosiglitazone maleate in accordance with the invention include, but are not limited to, agonists and antagonists for cell membrane receptors, neurotransmitters, toxins and venoms, viral epitopes, hormones, opiates, steroids, peptides, enzyme substrates and inhibitors, cofactors, drugs, lectins, sugars, oligonucleotides, nucleic acids, oligosaccharides, lipids, proteins, and analogs of any of the foregoing molecules.

The term "analog" refers to a molecule, which shares a common functional activity with the molecule to which it is deemed to be an analog and typically shares common structural features as well.

The term "recombinant" refers to any type of cloned biotherapeutic expressed in procaryotic cells or genetically engineered molecule, or combinatorial library of molecules which may be further processed into another state to form a second combinatorial library, especially molecules that contain protecting groups which enhance the physicochemical, pharmacological, and clinical safety of the biotherapeutic agent.

The term "vaccines" refers to therapeutic compositions for stimulating humoral and cellular immune responses, either isolated, or through an antigen presenting cell, such as an activated dendritic cell, that is able to activate T-cells to produce a multivalent cellular immune response against a selected antigen. The potent antigen presenting cell is stimulated by exposing the cell in vitro to a polypeptide complex. The polypeptide complex may comprise a dendritic cell-binding protein and a polypeptide antigen, but preferably, the polypeptide antigen is either a tissue-specific tumor antigen or an oncogene gene product. However, it is appreciated that other antigens, such as viral antigens can be used in such combination to produce immunostimulatory responses. In another preferred embodiment, the dendritic cell-binding protein that forms part of the immunostimulatory polypeptide complex is GM-CSF. In a further preferred embodiment, the polypeptide antigen that forms part of the complex is the tumor-specific antigen prostatic acid phosphatase. In still other preferred embodiments, the polypeptide antigen may be any one of the oncogene product peptide antigens. The polypeptide complex may also contain, between the dendritic cell-binding protein and the polypeptide antigen, a linker peptide. The polypeptide complex may comprise a dendritic cell-binding protein covalently linked to a polypeptide antigen, such polypeptide complex being preferably formed from a dendritic cell binding protein, preferably GM-CSF, and a polypeptide antigen. The polypeptide antigen is preferably a tissue-specific tumor antigen such as prostatic acid phosphatase (PAP), or an oncogene product, such as Her2, p21RAS, and p53; however, other embodiments, such as viral antigens, are also within the contemplation of the invention.

The term "immunoglobulins" encompasses polypeptide oligonucleotides involved in host defense mechanisms such as coding and encoding by one or more gene vectors, conjugating various binding moieties of nucleic acids in host defense cells, or coupling expressed vectors to aid in the treatment of a human or animal subject. The medicaments included in this class of polypeptides include IgG, IgE, IgM, IgD, either individually or in a combination with one another.

For purposes of the formulations of rosiglitazone maleate of this invention, which are intended for inhalation into the lungs, the medicament or drug is preferably micronized whereby a therapeutically effective amount or fraction (e.g., ninety percent or more) of rosiglitazone maleate or its combination drug is particulate. Typically, the particles have a diameter of less than about 10 microns, and preferably less than about 5 microns, in order that the particles can be inhaled into the respiratory tract and/or lungs.

The rosiglitazone maleate medicament is present in the inventive formulations in a therapeutically effective amount, that is, an amount such that the drug can be administered as a dispersion, aerosol, via oral or nasal inhalation, and cause its desired therapeutic effect, typically preferred with one dose, or through several doses. The drug is typically administered as an aerosol from a conventional valve, e.g., a metered dose valve, through an aerosol adapter also known as an actuator.

The term "amount" as used herein refers to a quantity or to a concentration as appropriate to the context. The amount of a drug that constitutes a therapeutically effective amount varies according to factors such as the potency of the particular drug, the route of administration of the formulation, and the mechanical system used to administer the formulation. A therapeutically effective amount of a particular drug can be selected by those of ordinary skill in the art with due consideration of such factors. Generally a therapeutically effective amount of rosiglitazone maleate will be from about 1 mg to about 500 mg based on 100 parts by weight of the fluid or propellant selected.

A suitable fluid includes air, a hydrocarbon such as n-butane, propane, isopentane, etc. or a propellant. A suitable propellant is any fluorocarbon, e.g. a 1–6 hydrogen containing flurocarbon (such as $CHF_2CHF_2$, $CF_3CH_2F$, $CH_2F_2CH_3$ and $CF_3CHFCF_3$), a perfluorocarbon, e.g. a 1–4 carbon perfluorocarbon, (such as $CF_3CF_3$, $CF_3CF_2CF_3$); or any mixture of the foregoing, having a sufficient vapor pressure to render them effective as propellants. Some typical suitable propellants include conventional chlorofluorocarbon (CFC) propellants, such as propellants 11, 12 and 114 or a mixture thereof. Non-CFC propellants, such as 1,1,1,2-tetrafluoroethane (Propellant 134a), 1,1,1,2,3,3,3-heptafluoropropane (Propellant 227) or a mixture thereof are preferred. The fluid or propellant is preferably present in an amount sufficient to propel a plurality of the selected doses of drug from an aerosol canister when such is employed.

A suitable stabilizer is selected. A suitable stabilizer includes (1) an amino acid selected from (a) a monoamino carboxylic acid of the formula, $H_2N$—R—COOH (I), (b) a monoamino dicarboxylic acid of the formula, $H_2N$—R $(COOH)_2$ (II) and (c) a diamino monocarboxylic acid of the formula $(H_2N)_2$—R COOH (III), where R is a straight or branched alkyl radical of from 1 to 22 carbon atoms, which can be mono or poly-substituted with moieties such as sulfide (—S—), oxide (—O—), hydroxyl (—OH), amide (—NH), sulfate (—SO4); aryl of the formula

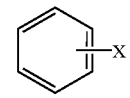

where X is hydrogen, halogen (F, Cl, BR, I), alkyl of 1 to 6 carbon atoms, alkoxy of 1 to 6 carbon atoms, hydroxy and nitro; and heterocyclic, such as thienyl, furyl, pyranyl, imidazolyl, pyrrolyl, thizolyl, oxazolyl, pyridyl, and pyrimidinyl compounds; (2) a derivative of the amino acid selected from (a) acid addition salts of the amino group, obtained from inorganic acids, such as hydrochloric, hydrobromic, sulfuric, nitric, phosphoric, and perchloric acids, as well as organic acids, such as tartaric, citric, acetic, succinic, maleic, fumaric, oxalic acids; (b) amides of the carboxylic acid group, e.g., glutamine, di-peptides, e.g. salts and esters of oxidized and unoxidized L-cysteinylglycine, gamma-L-glutamyl-L-cysteine, N-acetyl-L-cysteine-glycine, either conjugated, unconjugated or polymeric forms of L-Gly-L-Glu and L-Val-L-Thr, L-aspartyl-L-phenylalanine, muramyl dipeptides, nutrients such as L-tyrosyl-L-tyrosine, L-alanyl-L-tyrosine, L-arginyl-L-tyrosine, L-tyrosyl-L-arginine, N-Cbz-L-Leu-L-Leu-OCH and its salts or esters, glycyl-glycine, N-acetyl-L-aspartate-L-glutamate (NAAG), etc.; and tripeptides, e.g. oxidized and unoxidized gamma-L-glutamyl-L-cysteinylglycine; muramyl tripeptides, etc. (c) esters of the carboxylic acid group obtained from aliphatic straight or branched chain alcohols of from 1 to 6 carbon atoms, e.g. L-aspartyl-L-phenylalanine methylester (Aspartame®), (3) an ether of any of the foregoing; (4) a hydrate or semi-hydrate of any of the foregoing and (5) a mixture of the amino acid and the derivative of the amino acid.

Suitable amino acids of the formula I include glycine, alanine, valine, leucine, isoleucine, leucylalanine, methionine, threonine, isovaline, phenylalanine, tyrosine, serine, cysteine, N-acetyl-L-cysteine, histidine, tryptophan, proline, and hydroxyproline, e.g. trans-4-hydroxy proline. Compounds of the formula II include, aspartic acid, and glutamic acid, compounds of the formula (III) include arginine, glutamine, lysine, hydroxylysine, ornithine, asparagine, and citrulline.

A fluid or aerosol formulation preferably comprises the protective colloid stabilizer in an amount effective to stabilize the formulation relative to an identical formulation not containing the stabilizer, such that the drug does not settle, cream or flocculate after agitation so quickly as to prevent reproducible dosing of the drug. Reproducible dosing can be achieved if the formulation retains a substantially uniform drug concentration for about fifteen seconds to about five minutes after agitation.

For optimal functional and therapeutic performance of the aerosol formulation, either as a dry powder or as an aerosol suspension, the stabilizer is present either as a coarse carrier (e.g., 20–90 $\mu$m) or as a finely micronized powder, $\leq 10$ $\mu$m in diameter. In either case, reproducible drug dosimetry is obtained without the need to qualify the inspiratory maneuver of the patient. Accordingly, excellent dose uniformity is obtained at tidal flows of up to 2 liters, or at inspiratory flow rates of as low as 15 liters per minute to about 90 liters per minute.

The particular amount of stabilizer that constitutes an effective amount is dependent upon the particular stabilizer, the particular propellant, and on the particular drug used in the formulation. It is therefore not practical to enumerate specific effective amounts for use with specific formulations of the invention, but such amounts can readily be determined by those skilled in the art with due consideration of the factors set forth above. Generally, however, the stabilizer can be present in a formulation in an amount from about 0.001 parts per million to about 200,000 parts per million, more preferably about 1 part per million to about 10,000 parts per million, most preferably from about 10 parts per million to about 5,000 parts per million of the total formulation.

It has surprisingly been found that the formulation of the invention is stable without the necessity of employing a cosolvent, such as ethanol, or surfactants. However, further components, such as conventional lubricants or surfactants, cosolvents, ethanol, etc., can also be present in an aerosol formulation of the invention in suitable amounts readily determined by those skilled in the art. In this regard, reference is made to U.S. Pat. No. 5,225,183, which is incorporated hereinto by reference in its entirety.

Generally the formulations of the invention can be prepared by combining (i) the drug i.e. rosiglitazone maleate, in an amount sufficient to provide a plurality of therapeutically effective doses; (ii) the stabilizer in an amount effective to stabilize each of the formulations; (iii) the fluid or propellant in an amount sufficient to propel a plurality of doses, e.g. from an aerosol canister; and (iv) any further optional components e.g. ethanol as a cosolvent; and dispersing the components. The components can be dispersed using a conventional mixer or homogenizer, by shaking, or by ultrasonic energy. The components can also be dispersed using a bead mill or a microfluidizer. Bulk formulations can be transferred to smaller individual aerosol vials by using valve to valve transfer methods, pressure filling or by using conventional cold-fill methods. It is not required that a stabilizer used in a suspension aerosol formulation be soluble in the propellant. Those that are not sufficiently soluble can be coated onto the drug particles in an appropriate amount and the coated particles can then be incorporated in a formulation as described above.

Aerosol canisters equipped with conventional valves, preferably metered dose valves, can be used to deliver the formulations of the invention. It has been found, however, that selection of appropriate valve assemblies for use with aerosol formulations is dependent upon the particular stabilizer and other adjuvants used (if any), on the propellant, and on the particular drug being used. Conventional neoprene and buna valve rubbers used in metered dose valves for delivering conventional CFC formulations often have less than optimal valve delivery characteristics and ease of operation when used with formulations containing HFC-134a or HFC-227. Therefore certain formulations of the invention are preferably dispensed via a valve assembly wherein the diaphragm is made of a nitrile rubber such as DB-218 (American Gasket and Rubber, Schiller Park, Ill.) or an EPDM rubber such as Vistalon™ (Exxon), Royalene™ (UniRoyal), bunaEP (Bayer). Also suitable are diaphragms fashioned by extrusion, injection molding or compression molding from a thermoplastic elastomeric material such as FLEXOMER™ GERS 1085 NT polyolefin (Union Carbide).

Conventional aerosol canisters, coated or uncoated, anodized or unanodized, e.g., those of aluminum, glass, stainless steel, polyethylene terephthalate, and coated canisters or cans with epon, epoxy, etc., can be used to contain a formulation of the invention.

Conventional nebulizer systems can be employed with the formulations of this invention, as well as by powder aerosols.

The formulation of the invention can be delivered to the respiratory tract and/or lung by oral inhalation in order to effect bronchodilation or in order to treat a condition susceptible of treatment by inhalation, e.g., asthma, chronic obstructive pulmonary disease. The formulations of the invention can also be delivered by nasal inhalation in order to treat, e.g., allergic rhinitis, rhinitis, (local) or diabetes (systemic), or they can be delivered via topical (e.g., buccal) administration in order to treat, e.g., angina or local infection.

We claim:

1. A nonaqueous medicinal aerosol formulation, which comprises:

(a) a therapeutically effective amount of rosiglitazone maleate;

(b) a nonaqueous fluid propellant carrier for containing said medicament; and (c) a stabilizer selected from an amino acid, a derivative thereof, or a mixture of the foregoing.

2. The formulation as defined in claim 1 wherein said medicament is combined with a second medicament selected from the group consisting of an insulin analog, an amylin, an immunomodulating protein, an interleukin, an interferon, an erythropoietin, a heparin, a thrombolytic, an antitrypsin, an anti-protease, a hormone, a growth factor, an enzyme, a nucleic acid, an immunoglobulin, an antibiotic, an antiinfective, a calcitonin, a hematopoietic factor, a vaccine, a vasoactive peptide, an antisense agent, an oligonucleotide, DNase, a cyclosporin, ribavirin or a mixture of any of the foregoing medicaments.

3. The formulation as defined in claim 2 wherein said second medicament is selected from the group consisting of an insulin analog, an amylin, glucagon, octreotide, somatostatin, a calcitonin, an interferon, IgG, IgE, IgM, IgA, IgD, an interleukin, a gene; a vector, glucagon, acetohexamide, chlorpropamide, tolazemide, tolbutamide, glipizide, glyburide, glucophage, phentolamine, an oligonucleotide, ribavirin or a mixture of any of the foregoing medicaments.

4. The formulation as defined in claim 1 which further includes a cosolvent.

5. The formulation as defined in claim 4 wherein said cosolvent comprises ethanol.

6. A nonaqueous medicinal formulation, which consists essentially of:

(a) a therapeutically effective amount of rosiglitazone maleate combined with a second medicament selected from the group consisting of an insulin, an insulin analog, an amylin, an immunomodulating protein, an interleukin, an interferon, an erythropoietin, a heparin, a thrombolytic, an antitrypsin, an anti-protease, a hormone, a growth factor, an enzyme, a nucleic acid, an immunoglobulin, an antibiotic, an antiinfective, a calcitonin, a hematopoietic factor, a vaccine, a vasoactive peptide, an antisense agent, an oligonucleotide, DNase, a cyclosporin, ribavirin, glucagon, octreotide, somatostatin, IgG, IgE, IgM, IgA, IgD, an interleukin, a gene, a vector, acetohexamide, chlorpropamide, tolazemide, tolbutamide, glipizide, glyburide, glucophase, phentolamine or a mixture of any of the foregoing medicaments.

(b) a nonaqueous fluid propellant carrier for containing said medicament; and (c) a stabilizer selected from an amino acid, a derivative thereof, or a mixture of the foregoing.

7. The formulation as defined in claim 1 or claim 6 wherein said stabilizer is selected from the group consisting of the twenty essential and nonessential existing amino acids, any mixture thereof, and any derivative of the foregoing.

8. The formulation as defined in claim 1 or claim 6 wherein said stabilizer is selected from the group consisting of (1) a di-peptide selected from the group consisting of a salt and an ester of oxidized and unoxidized L-cysteinylglycine, gamma L-glutamyl-L-cysteine, N-acetyl-L-cysteine-glycine; (2) a conjugated, unconjugated or polymeric form-of L-Gly L-Glu and,L-Val-L-Thr; (3) L-aspartyl-L-phenylalanine; (4) a muramyl dipeptide; (5) a nutrient selected from the group consisting of L-tyrosyl-L-tyrosine, L-alanyl-L-tyrosine, L-arginyl-L-tyrosine, L-tyrosyl-L-arginine, N-Cbz-L-Leu-L-Leu-OCH and salts or esters of the foregoing; (6) glycylglycine; (7) N-acetyl-L-aspartate-L-glutamate; (NAAG) (8) a tripeptide selected from the group consisting of an oxidized and an unoxidized form of gamma-L-glutamyl-L-cysteinylglycine or a muramyl tripeptide and (9) a mixture of any of the foregoing stabilizers.

9. The formulation as defined in claim 1 or claim 6 wherein said fluid carrier is a propellant selected form the group consisting of 1,1,1,2-tetrafluoroethane, 1,1,1,2,3,3,3-heptafluoropropane or a mixture thereof.

10. The formulation as defined in claim 1 or claim 6 wherein said fluid carrier is a hydrocarbon propellant selected from the group consisting of n-butane, propane, isopentane or a mixture thereof.

11. The formulation as defined in claim 1 or claim 6 wherein said rosiglitazone maleate is present in a therapeutic amount ranging from 1 mg to 500 mg based on 100 parts by weight of the fluid carrier.

12. A method of treating in a human or an animal a condition capable of treatment by oral or nasal inhalation, which comprises, administering a formulation according to claim 1 or claim 6 to said human or animal by oral or nasal inhalation.

13. A formulation according to claim 1 or claim 6 in an aerosol canister equipped with a metered dose valve.

14. The formulation as defined in claim 1 or claim 6 wherein said stabilizer is present in an amount effective to prevent settling, creaming or flocculation of the formulation for a time sufficient to allow reproducible dosing of the drug after agitation of the formulation.

15. The formulation as defined in claim 14 wherein said stabilizer is present in an amount ranging from about 0.001 parts per million to about 200,000 parts per million of the total weight of the formulation.

16. A method of preparing a stable medicinal aerosol formulation according to claim 1 or claim 6 which comprises:

(a) combining (i) said rosiglitazone maleate medicament in an amount sufficient to provide a plurality of therapeutically effective doses, (ii) said fluid carrier in an amount sufficient to propel a plurality of said therapeutically effective doses; and (iii) said stabilizer in an amount effective to stabilize the formulation; and (b) dispersing components (i), (ii) and (iii).

17. The method as defined in claim 16 wherein the medicinal aerosol formulation further comprises combining in step (a) a cosolvent and in step (b) dispersing components (i), (ii) and (iii) with said cosolvent.

18. A method of stabilizing a nonaqueous suspension aerosol formulation comprising a nonaqueous propellant and rosiglitazone maleate medicament, which comprises, incorporating into the formulation a stabilizer selected from the group consisting of a suitable amino acid, a derivative thereof, or any mixture of the foregoing, in an amount which is effective to prevent settling, creaming, or flocculation of the formulation for a time sufficient to allow reproducible dosing of the drug after agitation of the formulation.

19. A metered dose inhaler containing a nonaqueous medicinal aerosol formulation, the formulation comprising:

(a) a rosiglitazone maleate medicament in a therapeutically effective amount;

(b) a nonaqueous propellant; and (c) a suitable stabilizer selected from an amino acid, an amino acid derivative, or a mixture of the foregoing, present in an amount sufficient to stabilize the formulation to prevent settling, creaming or flocculation for a time sufficient to allow reproducible dosing of the drug after agitation of the formulation.

20. The metered dose inhaler as defined in claim 19 wherein the stabilizer is selected from the group consisting of the twenty essential and nonessential existing amino acids, any mixture of any of the foregoing and any derivative of the foregoing.

21. A nonaqueous medicinal aerosol formulation, which consists essentially of:

(a) a therapeutically effective amount of rosiglitazone maleate;

(b) a nonaqueous fluid carrier for containing said medicament; and (c) a stabilizer selected from an amino acid, a derivative thereof, or a mixture of the foregoing.

* * * * *